US00PP24466P3

(12) United States Plant Patent
Cain

(10) Patent No.: US PP24,466 P3
(45) Date of Patent: May 20, 2014

(54) GRAPEVINE 'IFG THIRTEEN'

(50) Latin Name: *Vitis vinifera*
Varietal Denomination: IFG Thirteen

(75) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 39 days.

(21) Appl. No.: 13/507,753

(22) Filed: Jul. 26, 2012

(65) Prior Publication Data

US 2014/0033378 P1 Jan. 30, 2014

(51) Int. Cl.
*A01H 5/00* (2006.01)

(52) U.S. Cl.
USPC ..... Plt./205

(58) Field of Classification Search
CPC ..... A01H 5/0812
USPC ..... Plt./205
See application file for complete search history.

*Primary Examiner* — Annette Para

(57) ABSTRACT

This invention is a new and distinct grapevine variety denominated 'IFG Thirteen'. The new grapevine is characterized by producing obtuse ovate, completely black seedless berries which are firm in texture, low in acidity and ripen early in the growing season.

1 Drawing Sheet

Latin name of the genus and species claimed: *Vitis vinifera*. Variety denomination: 'IFG Thirteen'.

BACKGROUND OF THE INVENTION

The new and distinct grapevine described and claimed herein originated from a hand pollinated cross of the IS 283 variety (non-patented) and the Fantasy variety (non-patented) hybridized in May 2001. The abortive seed traces were subsequently embryo cultured and the resulting population of plants were planted in the field in April 2002. The present variety of grapevine was selected as a single plant in August 2003 and was first asexually propagated by hardwood cuttings in December 2003, near Delano, Kern County, Calif. The resulting propagules were planted during April 2004 near Delano, Kern County, Calif. and were found to reproduce true-to-type through at least three generations of asexual reproduction.

BRIEF SUMMARY OF THE INVENTION

The new grapevine 'IFG Thirteen' is characterized by producing obtuse ovate, completely black seedless berries which are firm in texture, low in acidity and ripen early in the growing season. Fruits normally ripen in late July to early August near Delano, Calif.

To the inventor's knowledge, the known variety which the new grapevine variety is most similar to is the 'IFG One' variety. 'IFG Thirteen' can be distinguished from the 'IFG One' variety by its producing slightly firmer, smaller berries (about 5.5 grams as opposed to about 6.1 grams for 'IFG One') that are slightly lower in acidity and slightly more obtuse in shape and are less prone to tip cracking and berry shatter. The 'IFG Thirteen' stores better than the 'IFG One' variety.

The 'IFG Thirteen' variety can be distinguished maternal parent the 'IS 283' variety by ripening slightly later, having firmer flesh, exhibiting less variability in berry size and having smaller residual seed traces.

The 'IFG Thirteen' variety can be distinguished from its paternal parent the Fantasy variety by producing smaller, less elongated, earlier ripening fruits that are less prone to splitting.

BRIEF DESCRIPTION OF THE FIGURE

The accompanying photographic illustration in FIG. 1 illustrates in full color 'IFG Thirteen'. The photograph was taken outdoors with indirect lighting. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Thirteen' plants grown in the vicinity of Delano, Kern County, Calif. during 2009 and 2010, and is believed to apply to plants of the variety grown under similar conditions of soil and climate elsewhere:

VINE

General:

*Size*.—Large.

*Vigor*.—Vigorous.

*Density of foliage*.—Dense.
*Productivity*.—Productive.
*Root stock*.—Own root.
*Training method*.—Typically spur pruned leaving 2 bud spurs.

Trunk:
*Trunk diameter of 7-year-old vines at 30 cm above the soil line*.—9.2 cm.
*Shape*.—Stocky.
*Straps*.—Long — split.
*Surface texture*.—Shaggy.
*Inner bark color*.—Greyed-orange 165A.

SHOOTS

Young shoot:
*Form of tip*.—Fully opened.
*Distribution of anthocyanin coloration of tip*.—Piping (striped).
*Intensity of anthocyanin coloration of tip*.—Weak.
*Density of prostrate hairs of tip*.—Sparse — Medium.
*Density of erect hairs of tip*.—Absent.
*Color*.—Can be either of the following colors; 146A, and B.

Woody shoot (mature canes):
*Shape*.—Medium.
*Internode length*.—Medium; About 12.4 cm.
*Width at node*.—About 1.2 cm.
*Cross section*.—Circular.
*Surface*.—Striate to slightly ribbed.
*Main color*.—Can be any of the following colors; Greyed orange; 165A, and B, and 164A, and B.
*Density of erect hairs of nodes*.—None.
*Density of erect hairs on internodes*.—None.
*Growth of axillary shoots*.—Medium; Approximately 12.7 cm.

Flowering shoot:
*Vigor during flowering*.—Strong.
*Attitude during flowering on shoots not tied*.—Semi-erect.
*Color*.—Dorsal side of internodes — Green with Red stripes.
*Color*.—Ventral side of internodes — Green.
*Color*.—Dorsal side of nodes — Green with Red stripes.
*Color*.—Ventral side of nodes — Green.
*Density of prostrate hairs on nodes*.—Sparse.
*Density of erect hairs on nodes*.—None.
*Density of prostrate hairs on internode*.—None.
*Density of erect hairs on internode*.—None.
*Anthocyanin coloration of buds*.—Present.

Tendrils:
*Distribution on the shoot* (*at full flowering*).—Discontinuous.
*Length of tendril*.—Medium; About 19.9 cm.
*Thickness*.—Medium.
*Color*.—Can be either of the following colors; Yellow — Green 152B, and N144A.
*Form*.—bifurcated.
*Number of consecutive tendrils*.—2.

LEAVES

Young leaves:
*Color of upper surface of first four distal unfolded leaves*.—Green.
*Average intensity of anthocyanin coloration of six distal leaves prior to flowering*.—Weak.
*Density of prostrate hairs between veins* (*lower surface*).—Very sparse.
*Density of prostrate hairs on veins* (*lower surface*).—Sparse.
*Density of erect hairs between veins* (*lower surface*).—Absent.
*Density of erect hairs on veins* (*lower surface*).—Very sparse.

Mature leaves:
*Average length*.—About 16.4 cm.
*Average width*.—About 19.7 cm.
*Mature leaf size*.—Large.
*Shape of blade*.—Pentagonal.
*Number of lobes*.—5.
*Anthocyanin coloration of main veins on upper side of blade*.—Very weak to weak.
*Mature leaf profile*.—Undulate.
*Blistering surface of blade upper surface*.—Weak.
*Leaf blade tip*.—Curved downwardly slightly.
*Undulation of margin*.—Medium.
*Thickness*.—Medium.
*Undulation of blade between main and lateral veins*.—Overall.
*Shape of teeth*.—Mixture of both sides straight and both sides convex.
*Length of teeth*.—Medium-long.
*Ratio length/width of teeth*.—Equal.
*Shape of upper lateral sinuses*.—Lobes slightly overlapping.
*Depth of upper lateral sinuses*.—Medium.
*General shape petiole sinus*.—Half open.
*Shape of base of upper leaf sinuses*.—V-shaped.
*Tooth at petiole sinus*.—Absent.
*Density of prostrate hairs between veins on lower surface of blade*.—Absent.
*Density if erect hairs between veins on lower surface of blade*.—Absent.
*Density of prostrate hairs on main veins on lower surface of blade*.—Very sparse.
*Density of erect hairs on main veins on lower surface of blade*.—Sparse.
*Density of prostrate hairs on main veins on upper surface of blade*.—Very sparse.
*Density of erect hairs on main veins on upper surface of blade*.—None.
*Autumn coloration of leaves*.—Leaves can be a single color or combination of colors, in a mottled pattern or on the edges of the leaves; Green; 139A, and Greyed-purple; N186A, and B, and 187A, and B.

Upper surface:
*Color*.—Green; 138A.
*Anthocyanin coloration of main veins*.—Very weak to weak.
*Surface appearance*.—Dull.
*Blistering surface of blade*.—Weak.

Lower surface:
*Color*.—Can be any of the following colors; Green; 138A, and B, and C.
*Anthocyanin coloration of main veins* (*lower surface*).—Weak.
*Glossiness*.—Medium.
*Surface texture*.—Smooth.
*Surface appearance*.—Semi-glossy.

Petiole:

*Length*.—About 15.6 cm.

*Length of petiole compared to middle vein*.—Slightly longer.

*Density of prostrate hairs on petiole*.—None.

*Density of erect hairs on petiole*.—Sparse.

Buds:

*Bud fruitfulness*.—Basal: Mostly fruitful.

*Position of first fruitful shoot on previous season cane*.—$1^{st}$-$2^{nd}$ node.

*Time of bud burst*.—Early; Mar. 14, 2012.

FLOWERS

General:

*Flower sex*.—Hermaphrodite.

*Length of first inflorescence*.—Medium; About 24.2 mm long by 13.8 mm wide.

*Position of first flowering and fruiting node*.—$4^{th}$ (current season growth).

*Number of inflorescence per flowering shoot*.—1.1 to 2.

*Time of bloom*.—Early as compared with similar varieties in the growing area of Delano, Calif.

*Date of full bloom*.—May 13, 2012.

FRUIT

General:

*Ripening period*.—Early; Approximately; Aug. 16, 2011.

*Use*.—Fresh market.

*Keeping quality*.—Good.

*Resistance to*.—Insects: Average typical of *Vitis vinifera* species. Diseases: Average typical of *Vitis vinifera* species.

*Refractometer test*.—Solid-sugar: About 15.6 Brix.

*Brix/acid*.—About 40.

*Titratable acidity*.—About 0.39.

*Juice pH*.—About 3.92.

Cluster:

*Mature cluster length* (*peduncle excluded*).—About 12.5 cm.

*Mature cluster width*.—About 16.8 cm.

*Mature cluster weight*.—About 1285 g.

*Bunch density*.—Medium.

*Number of berries*.—About 305.

*Form*.—Conical.

Peduncle:

*Lignification of peduncle*.—Weak.

*Length of peduncle*.—Medium; Approximately 4.7 cm.

Berry:

*Uniformity of size*.—Uniform.

*Single berry weight*.—About 5.5 g natural.

*Shape*.—Obtuse ovate.

*Seeds*.—Contains small rudimentary seed traces.

*Cross section*.—Circular.

*Berry dimensions*.—Longitudinal axis: About 2.6 cm. Horizontal axis: About 1.9 cm.

*Berry firmness*.—Medium firm.

*Particular flavor*.—Neutral.

*Bloom* (*cuticular wax*).—Medium.

*Berry separation from pedicel*.—Medium.

*Skin color* (*without bloom*).—Can be any of the following colors; Greyed-purple; N186A, and 187A.

Skin:

*Thickness*.—Medium.

*Texture*.—Medium.

*Reticulation*.—Absent.

*Tenacity*.—Tenacious to flesh.

What is claimed:

1. A new and distinct variety of grapevine as herein illustrated and described.

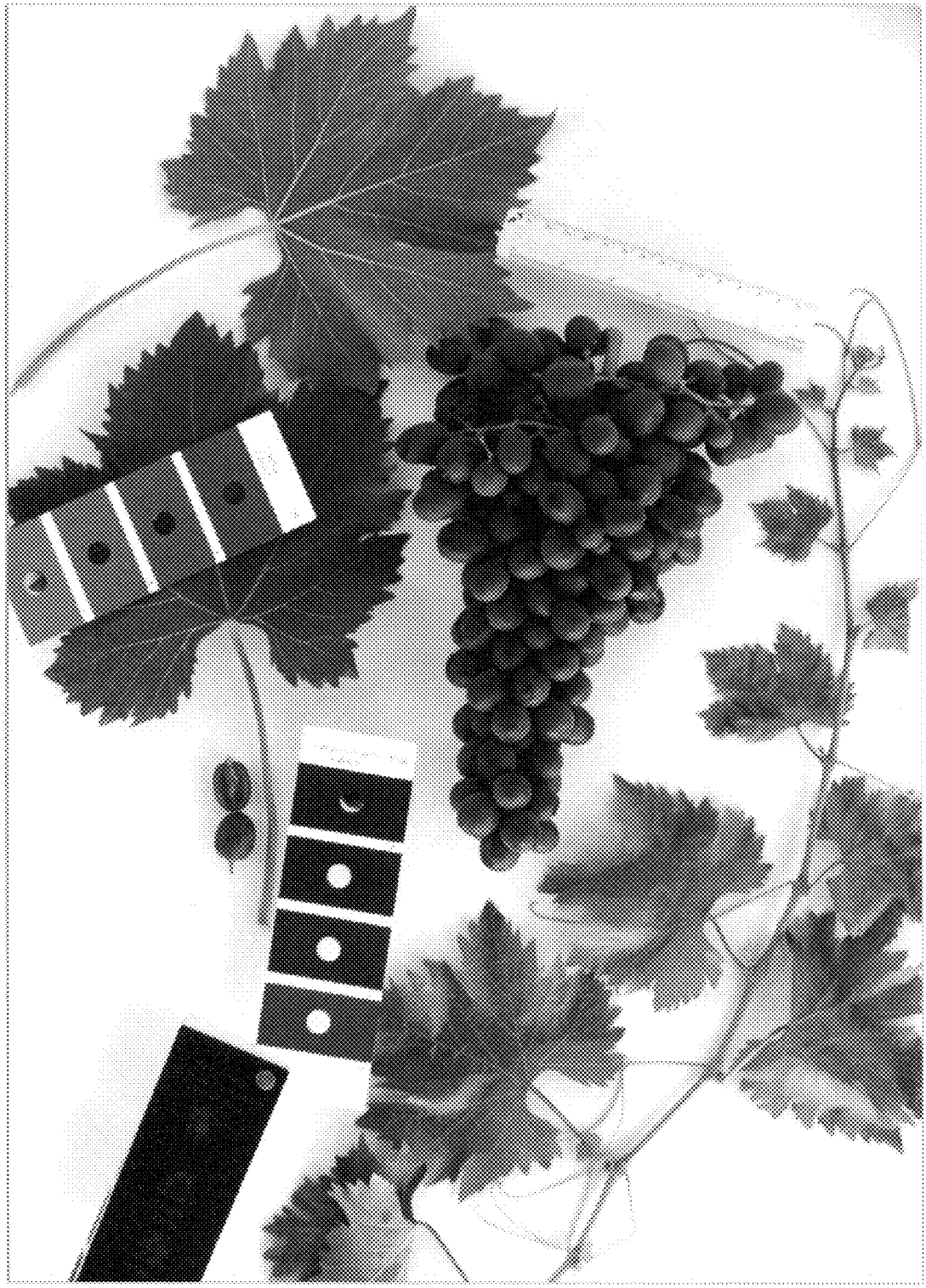

* * * * *